(12) United States Patent
Long et al.

(10) Patent No.: US 9,138,356 B2
(45) Date of Patent: Sep. 22, 2015

(54) WETNESS INDICATOR WITH HYDROPHANOUS ELEMENT FOR AN ABSORBENT ARTICLE

(71) Applicant: Kimberly-Clark Worldwide, Inc., Neenah, WI (US)

(72) Inventors: Andrew Mark Long, Appleton, WI (US); Shirlee Ann Weber, Neenah, WI (US); Jessica Sara Van Handel, Menasha, WI (US); Brooke Ashley Berg, Neenah, WI (US); Davis Dang Hoang Nhan, Appleton, WI (US); Darold Dean Tippey, Brunswick, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 432 days.

(21) Appl. No.: 13/748,262

(22) Filed: Jan. 23, 2013

(65) Prior Publication Data
US 2013/0138066 A1 May 30, 2013

Related U.S. Application Data

(62) Division of application No. 11/897,579, filed on Aug. 30, 2007, now Pat. No. 8,383,875.

(51) Int. Cl.
*A61F 13/511* (2006.01)
*A61F 13/42* (2006.01)
(52) U.S. Cl.
CPC ..................................... *A61F 13/42* (2013.01)
(58) Field of Classification Search
CPC .............. A61F 13/42; A61F 2013/422; A61F 2013/426–2013/427
USPC ..................................................... 604/361–362
See application file for complete search history.

(56) References Cited

U.S. PATENT DOCUMENTS 2,249,867 A * 7/1941 Snelling ..................... 73/335.08
3,675,654 A    7/1972 Baker et al.
(Continued)

FOREIGN PATENT DOCUMENTS

WO        WO 00/37009 A2    6/2000

OTHER PUBLICATIONS

Akin, Frank J. et al., "A Refined Method to Evaluate Diapers for Effectiveness in Reducing Skin Hydration Using the Adult Forearm," Skin Research and Technology, 1997, pp. 173-176.

*Primary Examiner* — Melanie Hand
*Assistant Examiner* — Paula L Craig
(74) *Attorney, Agent, or Firm* — Kimberly-Clark Worldwide, Inc.

(57) ABSTRACT

An absorbent article is provided for absorbing a liquid, the absorbent article including a chassis including a liner, an outer cover, and an absorbent structure positioned between the liner and the outer cover, the chassis including a front region and a back region, the front region and the back region defining a waist region therebetween. The absorbent article also includes a wetness indicator positioned adjacent the liner or the outer cover, the wetness indicator including a hydrophanous tissue layer having an absorbent-structure-facing side and being in liquid communication with the absorbent structure or the liner, and an indicator material disposed between the absorbent-facing side of the tissue layer and the absorbent structure. The absorbent article can also include a film layer disposed adjacent the tissue layer, and the indicator material can include an active constituent adapted to wick along the tissue layer when the absorbent article is insulted.

4 Claims, 8 Drawing Sheets

(56) References Cited

U.S. PATENT DOCUMENTS

| | | |
|---|---|---|
| 3,731,685 A | 5/1973 | Eidus |
| 3,759,261 A | 9/1973 | Wang |
| 4,100,324 A | 7/1978 | Anderson et al. |
| 4,192,311 A | 3/1980 | Felfoldi |
| 4,231,370 A | 11/1980 | Mroz et al. |
| 4,327,731 A | 5/1982 | Powell |
| 4,507,121 A | 3/1985 | Leung |
| 4,653,491 A | 3/1987 | Okada et al. |
| 4,681,576 A | 7/1987 | Colon et al. |
| 4,704,116 A | 11/1987 | Enloe |
| 4,705,513 A | 11/1987 | Sheldon et al. |
| 4,738,674 A | 4/1988 | Todd et al. |
| 4,931,051 A | 6/1990 | Castello |
| 4,940,464 A | 7/1990 | Van Gompel et al. |
| 5,284,703 A | 2/1994 | Everhart et al. |
| 5,350,624 A | 9/1994 | Georger et al. |
| 5,352,217 A | 10/1994 | Curro |
| 5,354,289 A | 10/1994 | Mitchell et al. |
| H1376 H | 11/1994 | Osborn, III et al. |
| 5,468,236 A | 11/1995 | Everhart et al. |
| 5,486,166 A | 1/1996 | Bishop et al. |
| 5,490,846 A | 2/1996 | Ellis et al. |
| 5,647,863 A | 7/1997 | Hammons et al. |
| 5,649,914 A | 7/1997 | Glaug et al. |
| 5,690,624 A | 11/1997 | Sasaki et al. |
| 5,766,212 A | 6/1998 | Jitoe et al. |
| 5,766,389 A | 6/1998 | Brandon et al. |
| H1746 H | 8/1998 | Carrier et al. |
| 5,820,973 A | 10/1998 | Dodge, II et al. |
| 6,075,178 A | 6/2000 | La Wilhelm et al. |
| 6,576,810 B1 | 6/2003 | Underhill et al. |
| 6,645,190 B1 | 11/2003 | Olson et al. |
| 6,657,100 B1 | 12/2003 | Underhill et al. |
| 6,710,221 B1 | 3/2004 | Pierce et al. |
| 6,747,185 B2 | 6/2004 | Inoue et al. |
| 7,154,019 B2 | 12/2006 | Mishima et al. |
| 7,306,764 B2 | 12/2007 | Mody |
| 7,718,844 B2 | 5/2010 | Olson |
| 7,982,090 B2 * | 7/2011 | Snauwaert et al. .......... 604/367 |
| 8,134,042 B2 | 3/2012 | Song et al. |
| 8,383,875 B2 * | 2/2013 | Long et al. .................. 604/361 |
| 2003/0158530 A1 | 8/2003 | Diehl et al. |
| 2004/0127867 A1 | 7/2004 | Odorzynski et al. |
| 2004/0191118 A1 | 9/2004 | Mody |
| 2004/0254549 A1 | 12/2004 | Olson et al. |
| 2005/0148961 A1 | 7/2005 | Sosalla et al. |
| 2006/0004333 A1 * | 1/2006 | Olson ........................ 604/361 |
| 2006/0069360 A1 | 3/2006 | Long et al. |
| 2006/0069362 A1 | 3/2006 | Odorzynski et al. |
| 2006/0114754 A1 * | 6/2006 | MacDonald et al. ......... 368/327 |
| 2006/0149198 A1 | 7/2006 | Liu |
| 2006/0229578 A1 | 10/2006 | Roe et al. |
| 2007/0142800 A1 | 6/2007 | Liu |
| 2008/0147030 A1 | 6/2008 | Nhan et al. |
| 2008/0228157 A1 * | 9/2008 | McKiernan et al. .......... 604/361 |

* cited by examiner

WETNESS INDICATOR WITH HYDROPHANOUS ELEMENT FOR AN ABSORBENT ARTICLE

PRIORITY

This application is a divisional of application Ser. No. 11/897,579, entitled Wetness Indicator with Hydrophanous Element for an Absorbent Article, and filed in the U.S. Patent and Trademark Office on Aug. 30, 2007. The entirety of the prior application is hereby incorporated by reference in this application.

BACKGROUND OF THE INVENTION

Absorbent articles such as diapers, training pants, incontinence products, feminine hygiene products, swim undergarments, and the like, conventionally include a liquid permeable body-side liner, a liquid impermeable outer cover, and an absorbent core. The absorbent core is typically located between the outer cover and the liner for taking in and retaining liquids (e.g., urine) exuded by the wearer. The absorbent core can be made of, for instance, superabsorbent particles. Many absorbent articles, especially those sold under the trade name HUGGIES™ by the Kimberly-Clark Corporation, are so efficient at absorbing liquids that it is sometimes difficult to tell whether or not the absorbent article has been insulted with a body fluid. It is especially difficult to tell whether or not the absorbent article has been insulted when the absorbent article is being worn by a newborn or other very young wearer. Insult amounts in such wearers tend to be very small. Other wearers might also produce very small insults.

Accordingly, various types of moisture or wetness indicators have been suggested for use in absorbent articles. The wetness indicators may include alarm devices that are designed to assist parents or attendants in identifying a wet diaper condition early on. These devices produce either a visual or an audible signal. Many of these devices rely on electronics, which may increase the expense of the absorbent article. Further, electronic devices rely on electrical sources and may be prone to failure if utilized for an extended period of time.

Problems, however, have been encountered in designing a signaling device that does not appreciably increase the cost of the absorbent article, while providing a meaningful signal to the caregiver without relying on an electrical source for operation. In addition, passive indicators located adjacent the outer cover of an absorbent article allow a caregiver to recognize when the absorbent article has been insulted, but such indicators typically require sufficient liquid to soak through the entire absorbent core of the absorbent article to reach the indicator on the inside of the outer cover before an indication can be produced.

SUMMARY OF THE INVENTION

The present inventors undertook intensive research and development efforts concerning improving absorbent articles, particularly with respect to providing a wetness indication when insult amounts are very small. The present disclosure presents a solution to the problems described above by providing a wetness indicator that is responsive to even very small insults. The wetness indicator needs only a small quantity of liquid insult to present an indication visible to the caregiver or wearer of the absorbent article while at the same time avoiding complex chemical or electrical indicators.

BRIEF DESCRIPTION OF THE DRAWINGS

The foregoing and other features and aspects of the present disclosure and the manner of attaining them will become more apparent, and the disclosure itself will be better understood by reference to the following description, appended claims and accompanying drawings.

Repeat use of reference characters in the present specification and drawings is intended to represent the same or analogous features or elements of the present disclosure.

DETAILED DESCRIPTION

It is to be understood by one of ordinary skill in the art that the present discussion is a description of exemplary aspects only, and is not intended as limiting the broader aspects of the present disclosure.

The present disclosure is generally directed to absorbent articles adapted to indicate the presence of a body fluid in the absorbent article or other changes in the condition of the product or wearer. The absorbent article may be, for instance, a diaper, a training pant, an incontinence product, a feminine hygiene product, a medical garment, a bandage, or the like. Generally, the absorbent articles are disposable, meaning that they are designed to be discarded after a limited use rather than being laundered or otherwise restored for reuse.

Figure 1:
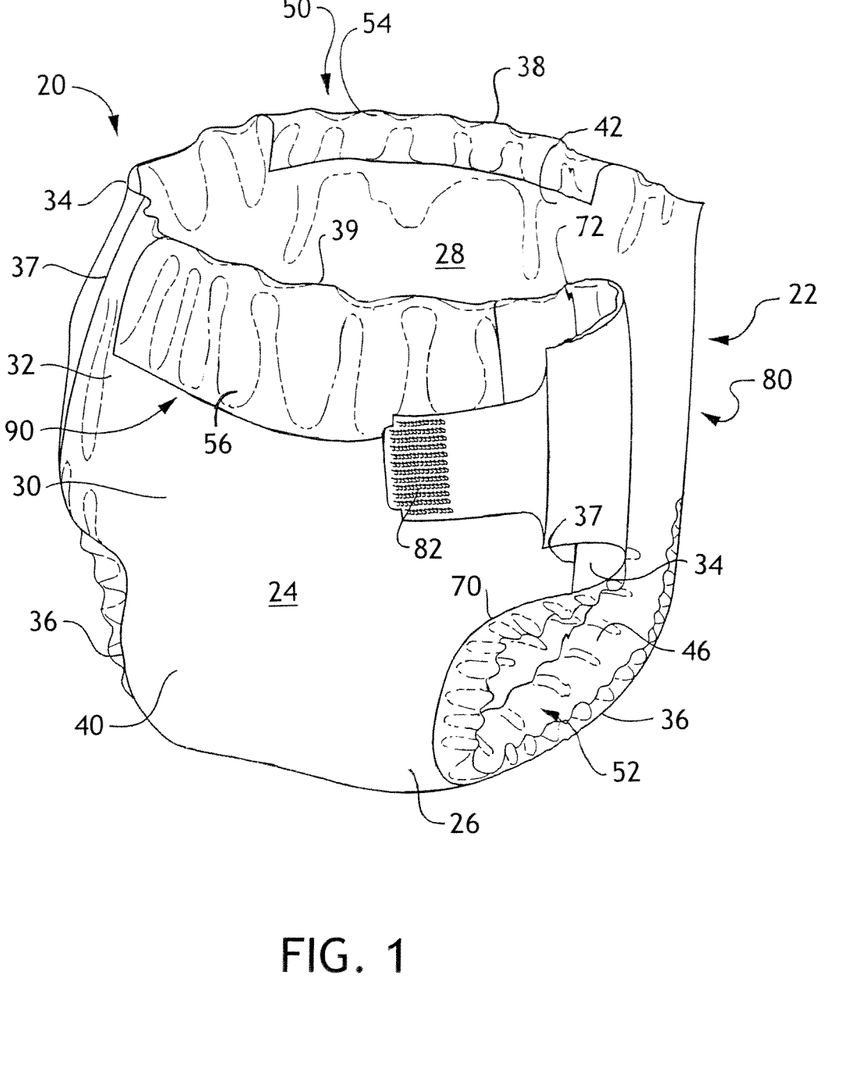
FIG. 1 is a rear perspective view of one aspect of an absorbent article.
Figure 2:
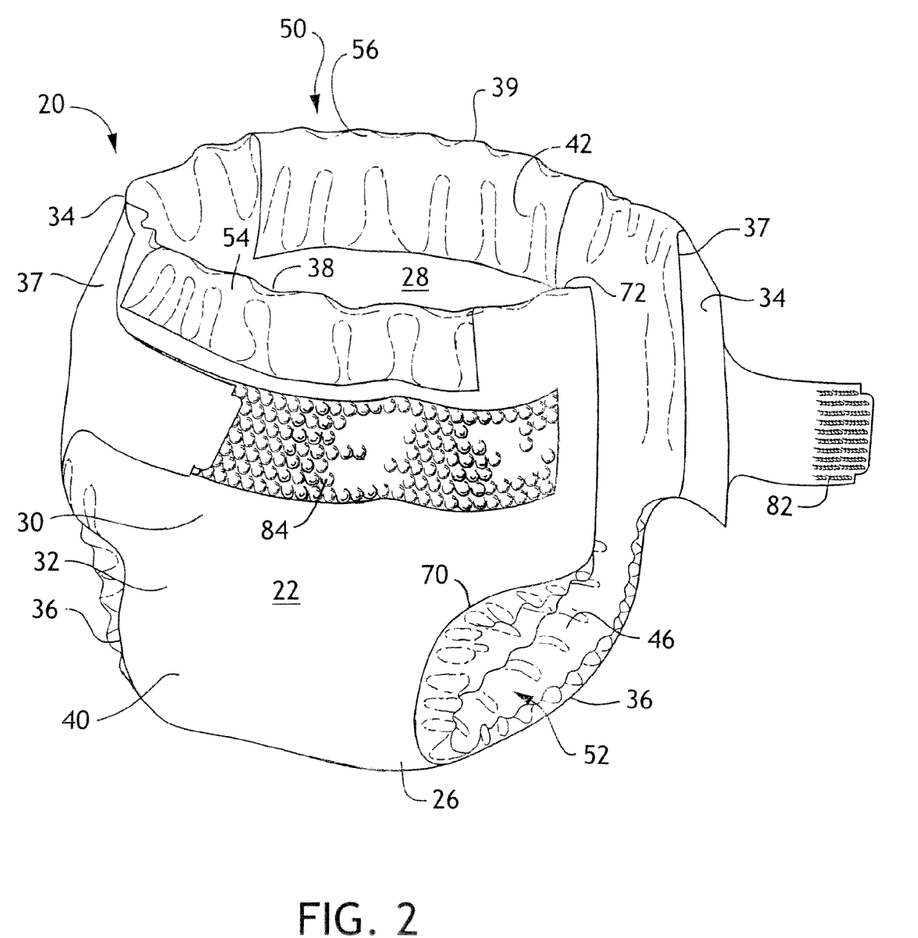
FIG. 2 is a front perspective view of the absorbent article illustrated in FIG. 1.

Referring to FIGS. 1 and 2, for exemplary purposes, an absorbent article 20 that may be made in accordance with the present disclosure is shown. The absorbent article 20 may or may not be disposable. It is understood that the present disclosure is suitable for use with various other absorbent articles intended for personal wear including, but not limited to, diapers, training pants, swim pants, feminine hygiene products, incontinence products, medical garments, surgical pads and bandages, other personal care or health care garments, and the like, without departing from the scope of the present disclosure.

By way of illustration only, various materials and methods for constructing absorbent articles such as the diaper 20 of the various aspects of the present disclosure are disclosed in PCT Patent Application WO 00/37009 published Jun. 29, 2000 by A. Fletcher et al.; U.S. Pat. No. 4,940,464 issued Jul. 10, 1990 to Van Gompel et al.; U.S. Pat. No. 5,766,389 issued Jun. 16, 1998 to Brandon et al., and U.S. Pat. No. 6,645,190 issued Nov. 11, 2003 to Olson et al. which are incorporated herein by reference to the extent they are consistent (i.e., not in conflict) herewith.

Figure 3:
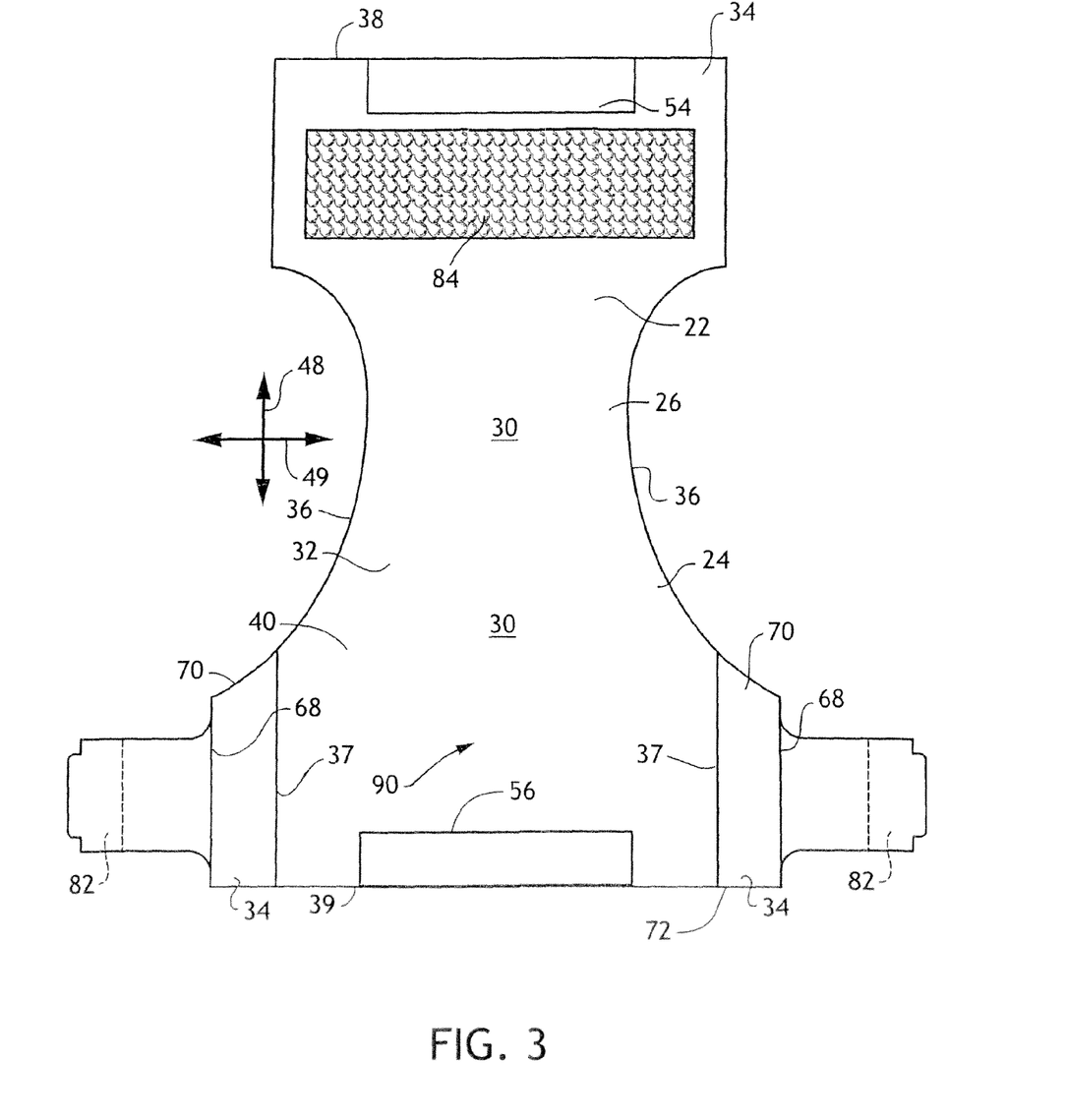
FIG. 3 is a plan view of the absorbent article shown in FIG. 1 with the article in an unfastened, unfolded and laid flat condition showing the surface of the article that faces away from the wearer.
Figure 4:
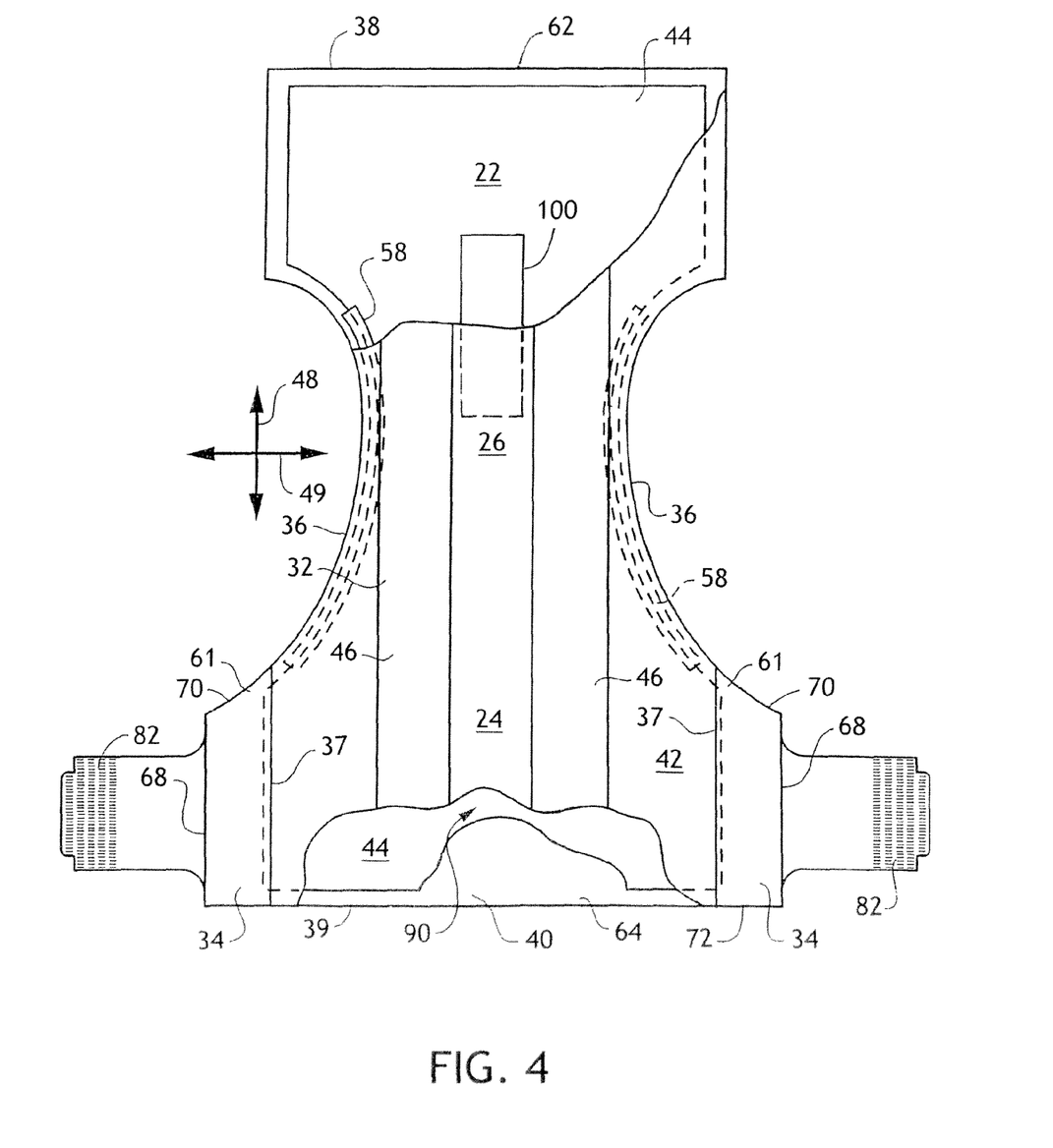
FIG. 4 is a plan view similar to FIG. 3 showing the surface of the absorbent article that faces the wearer when worn and with portions cut away to show underlying features.

A diaper 20 is representatively illustrated in FIG. 1 in a partially fastened condition. The diaper 20 shown in FIGS. 1 and 2 is also represented in FIGS. 3 and 4 in an opened and unfolded state. Specifically, FIG. 3 is a plan view illustrating the exterior side of the diaper 20, while FIG. 4 illustrates the interior side of the diaper 20. As shown in FIGS. 3 and 4, the diaper 20 defines a longitudinal direction 48 that extends from the front of the article, when worn. to the back of the article. Opposite to the longitudinal direction 48 is a lateral direction 49.

The diaper 20 defines a pair of longitudinal end regions, otherwise referred to herein as a front region 22 and a back region 24, and a center region, otherwise referred to herein as a crotch region 26, extending longitudinally between and interconnecting the front and back regions 22, 24. The diaper 20 also defines an inner surface 28 adapted in use (e.g., positioned relative to the other components of the article 20) to be disposed toward the wearer, and an outer surface 30 opposite the inner surface. The front and back regions 22, 24 are those portions of the diaper 20 which, when worn, wholly or partially cover or encircle the waist or mid-lower torso of the wearer. The crotch region 26 generally is that portion of the diaper 20 which, when worn, is positioned between the legs of the wearer and covers the lower torso and crotch of the wearer. The absorbent article 20 has a pair of laterally opposite side edges 36 and a pair of longitudinally opposite waist edges, respectively designated front waist edge 38 and back waist edge 39.

The illustrated diaper 20 includes a chassis 32 that, in this aspect, encompasses the front region 22, the back region 24, and the crotch region 26. Referring to FIGS. 1-4, the chassis 32 includes an outer cover 40 and a bodyside liner 42 (FIGS. 1 and 4) that may be joined to the outer cover 40 in a superimposed relation therewith by adhesives, ultrasonic bonds, thermal bonds or other conventional techniques. Referring to FIG. 4, the liner 42 may suitably be joined to the outer cover 40 along the perimeter of the chassis 32 to form a front waist seam 62 and a back waist seam 64. As shown in FIG. 4, the liner 42 may suitably be joined to the outer cover 40 to form a pair of side seams 61 in the front region 22 and the back region 24. The liner 42 can be generally adapted, i.e., positioned relative to the other components of the article 20, to be disposed toward the wearer's skin during use of the absorbent article. The chassis 32 may further include an absorbent structure 44 particularly shown in FIG. 4 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

The elasticized containment flaps 46 as shown in FIG. 4 define a partially unattached edge which assumes an upright configuration in at least the crotch region 26 of the diaper 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the diaper 20 may also suitably include leg elastic members 58 (FIG. 4), as are known to those skilled in the art. The leg elastic members 58 can be operatively joined to the outer cover 40 and/or the bodyside liner 42 and positioned in the crotch region 26 of the absorbent article 20.

The leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example, with the application of heat, such that elastic retractive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del., U.S.A.

In some aspects, the absorbent article 20 may further include a surge management layer that may be optionally located adjacent the absorbent structure 44 and attached to various components in the article 20, such as the absorbent structure 44 or the bodyside liner 42, by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166 issued Jan. 23, 1996 to David F. Bishop et al. and U.S. Pat. No. 5,490,846 issued Feb. 13, 1996 to Clifford J. Ellis et al. Other suitable surge management materials are described in U.S. Pat. No. 5,820,973 issued Oct. 13, 1998 to Richard N. Dodge II et al. The entire disclosures of these patents are hereby incorporated by reference herein to the extent they are consistent (i.e., not in conflict) herewith.

As shown in FIGS. 1-4, the absorbent article 20 further includes a pair of opposing elastic side panels 34 that are attached to the back region of the chassis 32. As shown particularly in FIGS. 1 and 2, the side panels 34 may be stretched around the waist and/or hips of a wearer in order to secure the garment in place. As shown in FIGS. 3 and 4, the elastic side panels are attached to the chassis along a pair of opposing longitudinal edges 37. The side panels 34 may be attached or bonded to the chassis 32 using any suitable bonding technique. For instance, the side panels 34 may be joined to the chassis by adhesives, ultrasonic bonds, thermal bonds, or other conventional techniques.

In an alternative aspect, the elastic side panels may also be integrally formed with the chassis 32. For instance, the side panels 34 may comprise an extension of the bodyside liner 42, of the outer cover 40, or of both the bodyside liner 42 and the outer cover 40.

In the aspects shown in the figures, the side panels 34 are connected to the back region of the absorbent article 20 and extend over the front region of the article when securing the article in place on a user. It should be understood, however, that the side panels 34 may alternatively be connected to the front region of the article 20 and extend over the back region when the article is donned.

With the absorbent article 20 in the fastened position as partially illustrated in FIGS. 1 and 2, the elastic side panels 34 may be connected by a fastening system 80 to define a three-dimensional diaper configuration having a waist opening 50 and a pair of leg openings 52. The waist opening 50 of the article 20 is defined by the waist edges 38 and 39 which encircle the waist of the wearer.

In the aspects shown in the figures, the side panels are releasably attachable to the front region 22 of the article 20 by the fastening system. It should be understood, however, that in other aspects, the side panels may be permanently joined to the chassis 32 at each end. The side panels may be permanently bonded together, for instance, when forming a training pant or absorbent swimwear.

The elastic side panels 34 each have a longitudinal outer edge 68, a leg end edge 70 disposed toward the longitudinal center of the diaper 20, and waist end edges 72 disposed toward a longitudinal end of the absorbent article. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present disclosure. As shown in FIG. 4, the outer edges 68 are generally parallel to the longitudinal direction 48 while the waist end edges 72 are generally parallel to the transverse axis 49. It should be understood, however, that in other aspects the outer edges 68 and/or the waist edges 72 may be slanted or curved as desired. Ultimately, the side panels 34 are generally aligned with a waist region 90 of the chassis.

The fastening system 80 may include laterally opposite first fastening components 82 adapted for refastenable engagement to corresponding second fastening components 84. In the aspect shown in the figures, the first fastening component 82 is located on the elastic side panels 34, while the second fastening component 84 is located on the front region 22 of the chassis 32. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the article 20 in its three-dimensional configuration.

The fastening components 82, 84 may be any refastenable fasteners suitable for absorbent articles, such as adhesive fasteners, cohesive fasteners, mechanical fasteners, or the like. In particular aspects, the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners. Alternatively, the first fastening components 82 may include loop fasteners and the second fastening components 84 may be complementary hook fasteners. In another aspect, the fastening components 82, 84 can be interlocking similar surface fasteners, or adhesive and cohesive fastening elements such as an adhesive fastener and an adhesive-receptive landing zone or material, or the like. One skilled in the art will recognize that the shape, density, and polymer composition of the hooks and loops may be selected to obtain the desired level of engagement between the fastening components 82, 84. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In the aspect shown in the figures, the fastening components 82 are attached to the side panels 34 along the edges 68. In this aspect, the fastening components 82 are not elastic or extendable. In other aspects, however, the fastening components may be integral with the side panels 34. For example, the fastening components may be directly attached to the side panels 34 on a surface thereof.

In addition to possibly having elastic side panels, the absorbent article 20 may include various waist elastic members for providing elasticity around the waist opening. For example, as shown in the figures, the absorbent article 20 can include a front waist elastic member 54 and/or a back waist elastic member 56.

The materials used to form the absorbent article 20 that surround the waist elastic members 54 and 56 may vary depending upon the particular application and the particular product being produced.

The outer cover 40, for instance, may be breathable and/or may be liquid impermeable. The outer cover 40 may be constructed of a single layer, multiple layers, laminates, spunbond fabrics, films, meltblown fabrics, elastic netting, microporous webs, bonded-carded webs or foams provided by elastomeric or polymeric materials. The outer cover 40, for instance, can be a single layer of a liquid impermeable material, or alternatively can be a multi-layered laminate structure in which at least one of the layers is liquid impermeable. In other aspects, however, it should be understood that the outer cover may be liquid permeable. In this aspect, for instance, the absorbent article may contain an interior liquid barrier layer.

For instance, the outer cover 40 can include a liquid permeable outer layer and a liquid impermeable inner layer that are suitably joined together by a laminate adhesive, ultrasonic bonds, thermal bonds, or the like. Suitable laminate adhesives, which can be applied continuously or intermittently as beads, a spray, parallel swirls, or the like, can be obtained from Bostik Findley Adhesives, Inc., of Wauwatosa, Wis., U.S.A., or from National Starch and Chemical Company, Bridgewater, N.J. U.S.A. The liquid permeable outer layer can be any suitable material and is desirably one that provides a generally cloth-like texture. One example of such a material is a 20 gsm (grams per square meter) spunbond polypropylene nonwoven web. The outer layer may also be made of those materials of which the liquid permeable bodyside liner 42 is made.

The inner layer of the outer cover 40 can be both liquid and vapor impermeable, or it may be liquid impermeable and vapor permeable. The inner layer can be manufactured from a thin plastic film, although other flexible liquid impermeable materials may also be used. The inner layer, or the liquid impermeable outer cover 40 when a single layer, prevents waste material from wetting articles, such as bed sheets and clothing, as well as the wearer and caregiver. A suitable liquid impermeable film for use as a liquid impermeable inner layer, or a single layer liquid impermeable outer cover 40, is a 0.02 millimeter polyethylene film commercially available from Pliant Corporation of Schaumburg, Ill., U.S.A.

The bodyside liner 42 is suitably compliant, soft-feeling, and non-irritating to the wearer's skin. The bodyside liner 42 is also sufficiently liquid permeable to permit liquid body exudates to readily penetrate through its thickness to the absorbent structure 44. A suitable bodyside liner 42 may be manufactured from a wide selection of web materials, such as porous foams, reticulated foams, apertured plastic films, woven and non-woven webs, or a combination of any such materials. For example, the bodyside liner 42 may include a meltblown web, a spunbonded web, or a bonded-carded web composed of natural fibers, synthetic fibers or combinations thereof. The bodyside liner 42 may be composed of a substantially hydrophobic material, and the hydrophobic material may optionally be treated with a surfactant or otherwise processed to impart a desired level of wettability and hydrophilicity.

The absorbent structure 44 may be disposed between the outer cover 40 and the bodyside liner 42. The absorbent structure 44 can be any structure or combination of components which are generally compressible, conformable, non-irritating to a wearer's skin, and capable of absorbing and retaining liquids and certain body wastes. For example, the absorbent structure 44 may include an absorbent web material of cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular aspect, the absorbent web material is a matrix of cellulosic fluff and superabsorbent hydrogel-forming particles. The cellulosic fluff may include a blend of wood pulp fluff. One preferred type of fluff is identified with the trade designation CR 1654, available from Bowater of Greenville, S.C., U.S.A., and is a bleached, highly absorbent sulfate wood pulp containing primarily southern soft wood fibers. The absorbent materials may be formed into a web structure by employing various conventional methods and techniques. For example, the absorbent web may be formed with a dry-forming technique, an air-forming technique, a wet-forming technique, a foam-forming technique, or the like, as well as combinations thereof. Methods and apparatus for carrying out such techniques are well known in the art. Furthermore, the absorbent structure may itself encompass multiple layers in the Z direction. Such multiple layers may take advantage of differences in absorbency capacity, such as by placing a lower capacity absorbent material layer closer to the liner 42 and a higher capacity absorbent material closer to the outer cover layer 40. Likewise, discrete portions of an absorbent single-layered structure may encompass higher capacity absorbents, and other discrete portions of the structure may encompass lower capacity absorbents.

As a general rule, the superabsorbent material is present in the absorbent web in an amount of from about 0 to about 90 weight percent based on total weight of the web. The web may have a density within the range of about 0.10 to about 0.60 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a superabsorbent material is capable of absorbing at least about 10 times its weight in liquid, and desirably is capable of absorbing more than about 25 times its weight in liquid. Suitable superabsorbent materials are readily available from various suppliers. For example, SXM 9394 and Favor 9543 superabsorbents are available from DeGussa Superabsorbers located at Parsippany, N.J. U.S.A.

After being formed or cut into a desired shape, the absorbent web material may be wrapped or encompassed by a wrap sheet made from a suitable tissue or meltblown web. The wrap sheet aids in maintaining the integrity and shape of the absorbent structure 44.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles, inorganic absorbent materials, treated polymeric staple fibers and the like. Any of a variety of synthetic polymers may be utilized as the melt-spun component of the coform material. For instance, in certain aspects, thermoplastic polymers can be utilized. Some examples of suitable thermoplastics that can be utilized include polyolefins, such as polyethylene, polypropylene, polybutylene and the like; polyamides; and polyesters. In one aspect, the thermoplastic polymer is polypropylene. Some examples of such coform materials are disclosed in U.S. Pat. No. 4,100,324 issued Jul. 11, 1978 to Richard A. Anderson, et al.; U.S. Pat. No. 5,284,703 issued Feb. 8, 1994 to Cherie H. Everhart, et al. and U.S. Pat. No. 5,350,624 issued Sep. 27, 1994 to William A. Georger, et al., which are incorporated herein by reference to the extent they are consistent (i.e., not in conflict) herewith.

When the absorbent article 20 is insulted with a liquid, such as urine, menses, blood, or the like, the absorbent structure 44 captures and retains the liquid. Conventional absorbent articles 20 are so effective at retaining liquid that caregivers may not know when an absorbent article 20 has been insulted. With traditional products, the caregiver does not have any way of determining whether the absorbent article 20 has been insulted, especially with younger wearers of the absorbent article 20 because insults from younger wearers tend to be quite small. A body fluid indication system including a wetness indicator 100 that is in liquid communication with either the absorbent structure 44, the liner 42, or both, addresses these issues.

The present disclosure is directed to incorporating a body-fluid-indicating system into a disposable absorbent article 20. In this regard, as best illustrated in FIGS. 5-11, the absorbent article 20 includes a wetness indicator 100 positioned adjacent the liner 42. The body-fluid-indicating system is described herein in relation to the liner 42, but in other aspects the body-fluid-indicating system can be associated instead with the outer cover 40, with appropriate changes made to the description.

The wetness indicator 100 includes a tissue layer 104. At least a portion of the tissue layer 104 of the wetness indicator 100 is in liquid communication with either the absorbent structure 44, the liner 42, or both. The tissue layer 104 of the wetness indicator 100 may be in direct contact with the absorbent structure 44. Alternatively, intermediate materials such as a surge management layer may be interposed between the tissue layer 104 of the wetness indicator 100 and the absorbent structure 44. The tissue layer 104 has an absorbent-structure-facing side and a liner-facing side.

The tissue layer 104 may be any suitable material, such as a tissue, nonwoven layer, cellulosic materials, treated nonwovens, synthetic fibers, natural fibers, open-celled foam, or the like. Suitable material and construction of the tissue layer 104 may be chosen such that a liquid will move slowly through the tissue layer 104. This speed at which a liquid moves through the tissue layer 104 may be measured using the vertical wicking test as described below. The tissue layer 104 may have a vertical wicking speed of less than approximately 1.0 cm/min, alternatively less than approximately 0.5 cm/min, or alternatively less than approximately 0.1 cm/min. Low wicking speed of tissue layer 104 allows for relatively short wetness indicators 100 to be utilized to indicate relatively long durations from the time of insult.

The wetness indicator 100 further includes an indicator material 108 located with the wetness indicator 100. The indicator material 108 can be printed or applied by any other suitable method to one of the tissue layer 104, first film layer 102, second film layer 103, or absorbent structure 44. The indicator material is preferably located between the absorbent-facing side of the tissue layer 104 and the absorbent structure, inclusive. In one aspect of the present disclosure, the indicator material 108 may be disposed on the absorbent-facing side of the tissue layer 104. Other arrangements are discussed below.

The film layers 102, 103 may be breathable or non-breathable and are generally translucent or transparent. The film layers 102, 103 are generally liquid-impermeable and are selected such that they do not significantly affect the TEWL (i.e., trans-epidermal water loss as measured using an evaporimeter; see, e.g. F. J. Akin, J. T. Lemmen, D. L. Bozarth, M. J. Garafalo, and G. L. Grove (1997) "A Refined Method to Evaluate Diapers for Effectiveness in Reducing Skin Hydration Using the Adult Forearm" Skin Research and Technology Vol. 3, 173-176, which is hereby incorporated by reference in its entirety in a manner consistent herewith) of the absorbent article 20 in an adverse manner. The film layers 102, 103 can be constructed from, for example, polyethylene, polypropylene, polyester, or any material with similar properties. The film layers 102, 103 can be breathable or non-breathable and may be perforated or apertured or intentionally punctured if desired. The film layers 102, 103 may also be a continuous strip or non-continuous if desired, or several strips or sections of film can also be used.

The wetness indicator 100 further includes an indicator material 108 located with the wetness indicator 100. The indicator material 108 can be printed or applied by any other suitable method to one of the tissue layer 104, first film layer 102, second film layer 103, or absorbent structure 44. The indicator material is preferably located between the absorbent-facing side 105 of the tissue layer 104 and the absorbent structure, inclusive. In one aspect of the present disclosure, the indicator material 108 may be disposed on the absorbent-facing side 105 of the tissue layer 104. Other arrangements are discussed below.

The indicator material 108 may be printed or otherwise applied to the tissue layer 104. The indicator material 108 should be permanent in the respect that the indicator material 108 should not dissolve or otherwise be removed from the tissue layer 104 when the tissue layer 104 is wetted. The color and darkness of the indicator material 108 is selected such that the indicator material 108 is generally invisible to a viewer through the tissue layer 104, film layer 102, and liner 42 when the tissue layer 104 is dry, but visible to a viewer through those structures when the tissue layer 104 is wetted. The indicator material 108 can, for example, be printed onto the tissue layer or film layer or surge or other material.

In another aspect of the present disclosure, a printed material 110 and an indicator material 108 may be selected such that the printed material 110 is generally visible to a viewer through the tissue layer 104, film layer 102, and liner 42 when the tissue layer 104 is dry, while the indicator materials 108 is generally invisible to a viewer through the tissue layer 104, film layer 102, and liner 42 when the tissue layer 104 is dry. In this aspect, both the printed material 110 and the indicator material 108 will be visible to a viewer through those structures when the tissue layer 104 is wetted. The printed material 110 may be printed or otherwise applied to either the absorbent-structure-facing side or the liner-facing side of the tissue layer 104, or to both sides.

In another aspect of the present disclosure, the indicator material 108 is applied to the tissue layer 104 in a wavy or random pattern to reduce the visibility of the indicator material 108 through the liner 42 when the tissue layer 104 is dry.

In still another aspect of the present disclosure, the indicator material 108 includes a plurality of active constituents, such that the active constituents move along the wetness indicator 100 at different speeds as a liquid moves through the wetness indicator 100. The indicator material 108 can include constituents that move along the tissue layer 104 in a chromatographic manner. An active constituent as used herein is defined as a portion of the indicator material 108 that is detectable by the caregiver, either alone, or in combination with another portion of the absorbent article 20. For example, an active constituent may be detected visibly (e.g. colored), alternatively, an active constituent may be detected tactilely or audibly, when it comes in contact with a second material in the absorbent article.

The indicator material 108 may be a solid or liquid. For example, the indicator material 108 may be an ink where the plurality of active constituents include a first active constituent of a first color and a second active constituent of a second color. The first color and the second color may be different from one another. For example, the first color may be blue and the second color may be yellow. In this example, before liquid moves through the wetness indicator 100, the indicator material 108 may appear as a single green mark. As liquid begins to move through the wetness indicator 100, the yellow constituent may move more quickly than the blue constituent. By selecting the size of the molecules and the chemical components that make up the molecules of the colored constituent, the speed at which the active constituents move may be adjusted. For example, the yellow constituent may move at a relatively high speed, such that the wetness indicator 100 quickly becomes yellow along the entire length upon a first insult. The blue constituent may move more slowly such that a single insult will only move the blue constituent a fraction, for example, one-quarter of the way along the wetness indicator 100. In this way, a single indicator material 108 may have dual functions, indicating whether or not the article has been insulted, as well as indicating the degree to which the absorbent structure 44 has been utilized.

The indicator material 108 may include active constituents that do not move along the wetness indicator 100 when the liquid moves through the wetness indicator 100. In this way, the "stationary" active constituent is a reference mark to which the constituents that move may be compared. This may simplify manufacture of the absorbent article 20, in that the indicator material 108 need not be registered to additional marks on the article 20.

In another aspect of the present disclosure, an image layer 114 may be interposed at some point between the tissue layer and the absorbent structure. If the image layer 114 is present, the indicator material 108 is applied to or disposed on a liner-facing side of the image layer 114 so that the indicator material becomes visible through the liner 42 when the tissue layer 104 is wetted.

Various aspects of the present disclosure are representatively illustrated in FIGS. 5-11. These examples are not meant to be limiting but are illustrative of some of the possible arrangements of the elements between the liner 42 and the absorbent structure 44. The figures are also not intended to illustrate or limit the relative size, thickness, density, or spacing of any element or combination of elements. In each figure, the arrangement will be described in order from the liner 42 to the absorbent structure 44.

Figure 5:
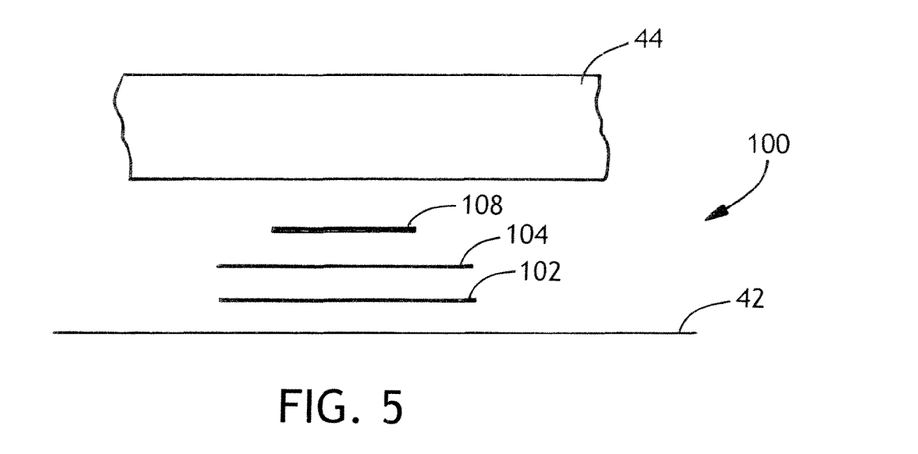
FIG. 5 is a cross sectional exploded schematic view of an aspect showing portions of a liner, an absorbent structure, and a wetness indicator.
Figure 6:
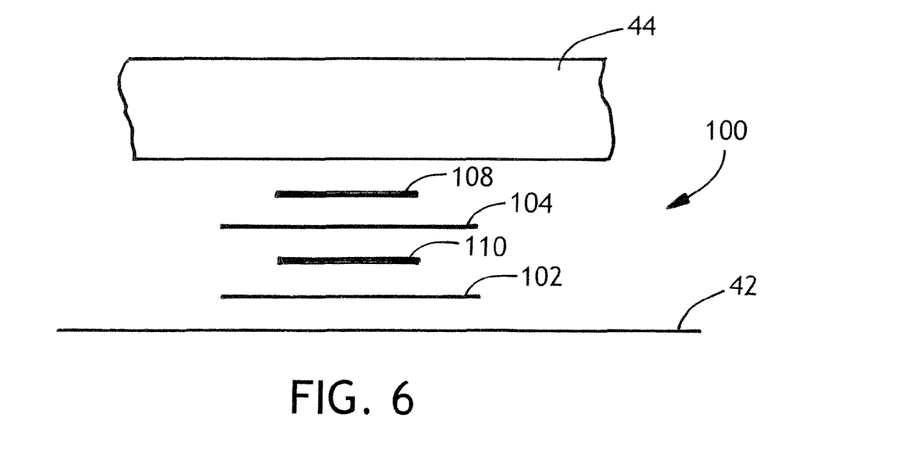
FIG. 6 is a cross sectional exploded schematic view of an aspect showing portions of a liner, an absorbent structure, and a wetness indicator.

FIG. 5 shows the first film layer 102 adjacent the liner 42, the tissue layer 104 adjacent the first film layer 102, and the indicator material 108 disposed between the tissue layer 104 and the absorbent structure 44. The indicator material 108 may be applied to either of the tissue layer 104 or the absorbent structure 44. FIG. 6 shows the same structure as FIG. 5 with the addition of printed material 110 disposed between the first film layer 102 and the tissue layer 104. The printed material 110 can be applied to either of the first film layer 102 and the tissue layer 104. In an alternative arrangement not shown, the printed material 110 may be disposed between the liner 42 and the first film layer 102 and applied to either of these. The printed material may also be applied to the body-facing side of the liner 42 (not shown). In other aspects of the present disclosure, the printed material 110 can be added to any of the arrangements illustrated in FIGS. 5-11.

Figure 7:
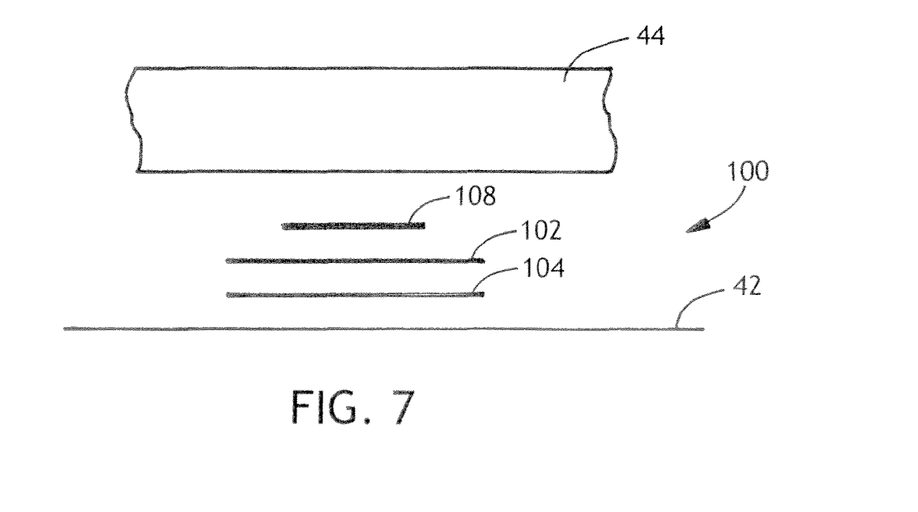
FIG. 7 is a cross sectional exploded schematic view of an aspect showing portions of a liner, an absorbent structure, and a wetness indicator.
Figure 8:
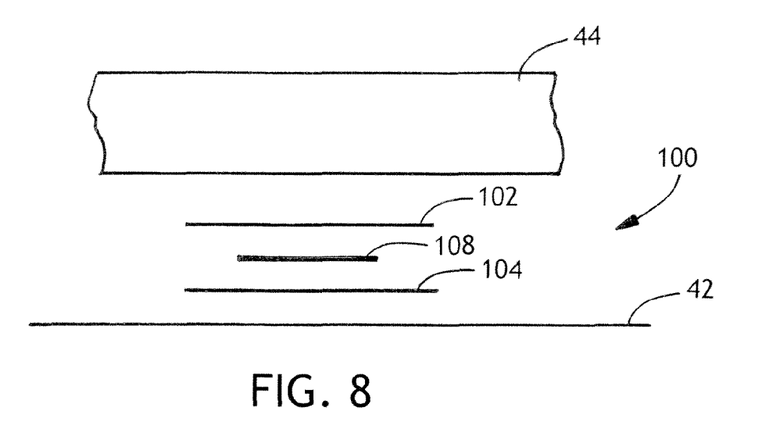
FIG. 8 is a cross sectional exploded schematic view of an aspect showing portions of a liner, an absorbent structure, and a wetness indicator.

FIG. 7 shows tissue layer 104 adjacent the liner 42, the first film layer 102 adjacent the tissue layer 104, and the indicator material 108 disposed between the first film layer 102 and the absorbent structure 44. The indicator material 108 may be applied to either of the first film layer 102 or the absorbent structure 44. FIG. 8 shows tissue layer 104 adjacent the liner 42, the indicator material 108 disposed adjacent the tissue layer 104, and the first film layer 102 disposed between the indicator material 108 and the absorbent structure 44. The indicator material 108 may be applied to either of the tissue layer 104 or the first film layer 102.

Figure 9:
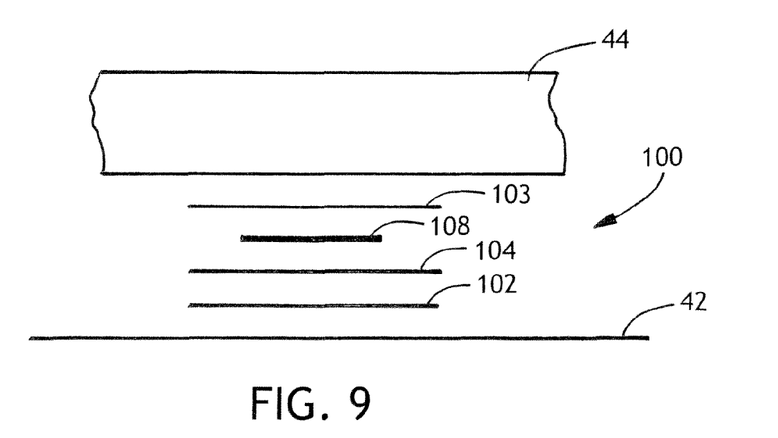
FIG. 9 is a cross sectional exploded schematic view of an aspect showing portions of a liner, an absorbent structure, and a wetness indicator.
Figure 10:
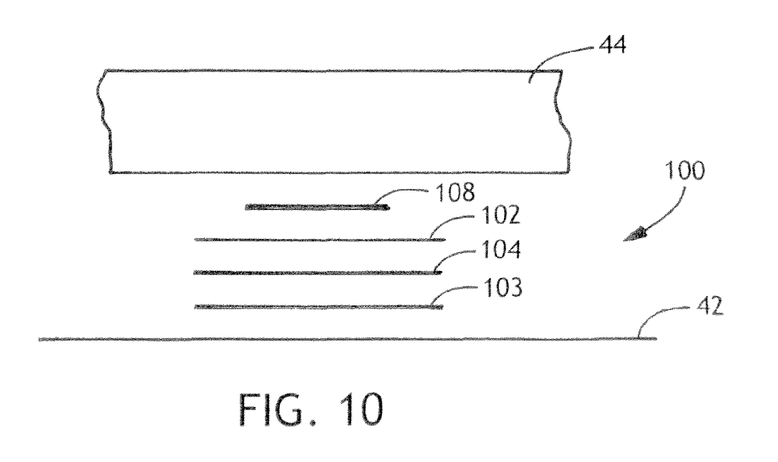
FIG. 10 is a cross sectional exploded schematic view of an aspect showing portions of a liner, an absorbent structure, and a wetness indicator.
Figure 11:
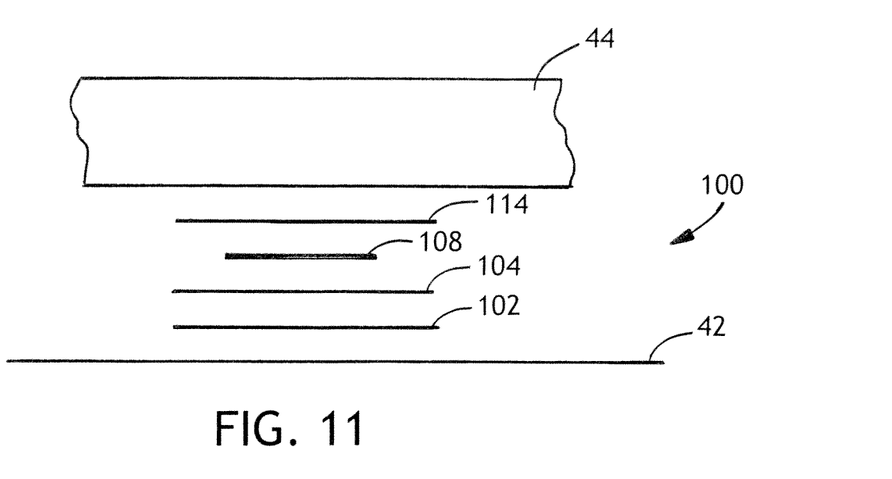
FIG. 11 is a cross sectional exploded schematic view of an aspect showing portions of a liner, an absorbent structure, and a wetness indicator.

FIG. 9 shows the same structure as FIG. 5 with the addition of the second film layer 103 disposed between the indicator material 108 and the absorbent structure 44. FIG. 10 shows the same structure as FIG. 7 with the addition of the second film layer 103 disposed between the liner 42 and the tissue layer 104. Finally, FIG. 11 shows the same structure as FIG. 5 with the addition of the image layer 114 disposed between the indicator material 108 and the absorbent structure 44. In this aspect, the indicator material 108 is applied to or disposed on the liner-facing side of the image layer 114. Similar modifications can be made to the structures of FIGS. 7-10 to add the image layer 114 adjacent the indicator material 108 to provide a surface upon which the indicator material 108 can be applied or otherwise disposed.

In use, the tissue layer 104 wicks liquid along its length such that more of the wetness indicator 100 is used. The tissue layer 104 is designed to be hydrophanous in that the tissue layer 104 is generally opaque or of limited translucence when dry and translucent or transparent when wetted with a liquid. The term "translucent" generally refers to permitting the passage of light, both in the sense of being transparent, in which objects may be seen clearly therethrough, and in the sense that light may be transmitted and diffused such that objects are not seen clearly therethrough. The specific material and properties of the tissue layer 104 are selected such that the indicator material 108 is generally invisible or of limited visibility to a viewer through the tissue layer 104, film layer 102, and liner 42 when the tissue layer 104 is dry, but visible to a viewer through those structures when the tissue layer 104 is wetted. If the basis weight of the tissue layer 104 is too low, the tissue layer 104 will not adequately wick liquid along its length, and the indicator material 108 may be visible when the tissue layer 104 is dry. If the basis weight of the tissue layer 104 is too high, the tissue layer 104 might not become translucent or transparent enough when wetted to make the indicator material 108 visible. The tissue layer 104 can be constructed from, for example, UCTAD (uncreped through-air dried technology), CTEC (conventional technology), printed creped uncreped through-air dried technology, or DRC (double re-creped) tissues or any tissue with similar properties, including commercially-available towels, bath tissues, or facial tissues.

Figure 12:
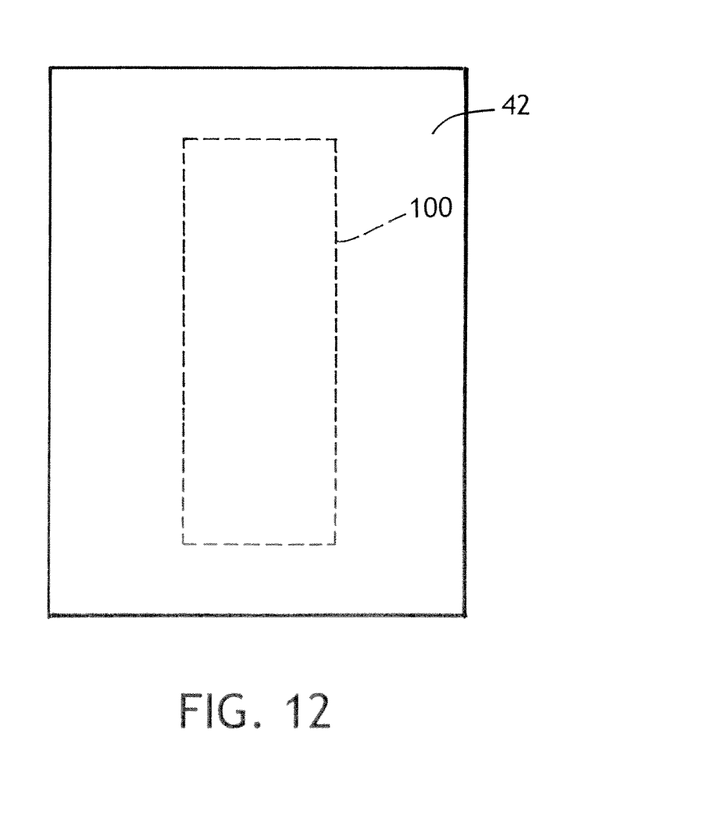
FIG. 12 is a plan schematic view of an aspect of a liner and a wetness indicator prior to insult.
Figure 13:
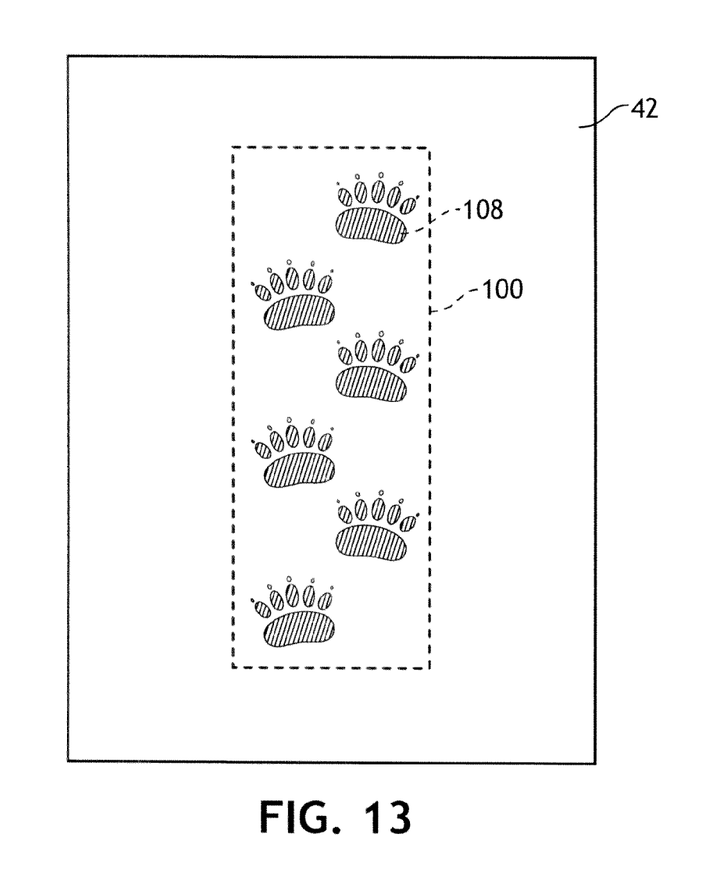
FIG. 13 is a plan schematic view of another aspect of a liner and a wetness indicator prior to insult.
Figure 14:
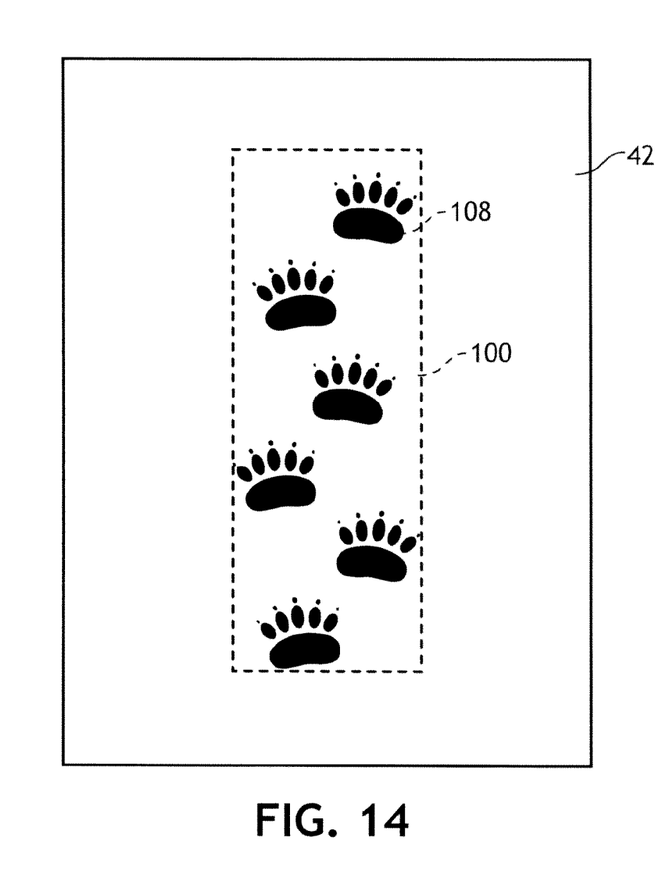
FIG. 14 is a plan schematic view of an aspect of a liner and a wetness indicator after insult.

The functioning of the wetness indicator 100 is further illustrated in FIGS. 12-14. FIG. 12 illustrates what one might observe as one views the liner from the body-facing side of the absorbent article 20 prior to insult of the absorbent article 20. One might see a vague outline of the wetness indicator 100 through the liner 42, but the indicator material 108 on the tissue layer 104 is generally not visible due to the generally opaque nature of the tissue layer 104 prior to insult. In other aspects, depending primarily on the basis weights of the liner 42, the film layer 102, and the tissue layer 104, and on the type of indicator material 108 chosen, the indicator material 108 might be partially visible prior to insult as illustrated in FIG. 13. After insult, however, the indicator material 108 is easily visible as illustrated in FIG. 14 due to the hydrophanous nature of the tissue layer 104. The indicator material 108 might or might not be at least partially visible prior to insult as long as a clear differentiation is made between the pre- and post-insult views of the indicator material 108.

All or a portion of the liner 42 adjacent the wetness indicator 100 may be translucent to facilitate detection of the wetness indicator 100 and active constituents. Alternatively, all or a portion of the liner 42 adjacent the wetness indicator 100 may be transparent.

In other aspects of the present disclosure, the absorbent article 20 includes a wetness indicator 100 positioned adjacent the outer cover 40. Any of the aspects, arrangements, and structures described herein may be applied to a wetness indicator 100 adjacent the outer cover 40 instead of the liner 42. The indicator material 108 would consequently be visible through the outer cover 40 following an insult in much the same way as otherwise described herein.

These and other modifications and variations to the present disclosure may be practiced by those of ordinary skill in the art, without departing from the spirit and scope of the present disclosure, which is more particularly set forth in the appended claims. In addition, it should be understood that aspects of the various aspects may be interchanged both in whole or in part. Furthermore, those of ordinary skill in the art will appreciate that the foregoing description is by way of example only, and is not intended to limit the disclosure as further described in such appended claims.

What is claimed is:

1. An absorbent article for absorbing a liquid, the absorbent article comprising:
 a chassis including a liner, an outer cover, and an absorbent structure positioned between the liner and the outer cover, the chassis including a crotch region positioned in between a front region and a back region, the front region and the back region defining a waist region therebetween;
 a wetness indicator positioned adjacent the liner, the wetness indicator including a tissue layer having a liner-facing side and an absorbent-structure-facing side and being in liquid communication with the absorbent structure or the liner, a film layer positioned between the liner and the absorbent structure, and an indicator material including an active constituent adapted to wick along the tissue layer when the absorbent article is insulted.

2. The absorbent article of claim 1, wherein the indicator material includes a plurality of active constituents, wherein the active constituents move along the tissue layer at different speeds as liquid moves along the tissue layer, and wherein the plurality of active constituents includes a visible constituent.

3. The absorbent article of claim 1, wherein the indicator material includes a plurality of active constituents, and the plurality of active constituents includes a first active constituent of a first color and a second active constituent of a second color, the first color and the second color being different from one another.

4. The absorbent article of claim 1, wherein the indicator material includes a plurality of active constituents, and at least one of the plurality of active constituents does not move along the tissue layer when the liquid moves along the tissue layer.

* * * * *